US012702558B2

(12) United States Patent
Frock et al.

(10) Patent No.: US 12,702,558 B2
(45) Date of Patent: Aug. 11, 2026

(54) POROUS FUSION DEVICE

(71) Applicant: Spinal Simplicity, LLC, Overland Park, KS (US)

(72) Inventors: Adam Frock, Lenexa, KS (US); Adam Rogers, Olathe, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 46 days.

(21) Appl. No.: 18/766,125

(22) Filed: Jul. 8, 2024

(65) Prior Publication Data

US 2025/0025308 A1 Jan. 23, 2025

Related U.S. Application Data

(60) Provisional application No. 63/528,197, filed on Jul. 21, 2023.

(51) Int. Cl.
*A61F 2/30* (2006.01)
*A61F 2/28* (2006.01)
*A61F 2/44* (2006.01)

(52) U.S. Cl.
CPC ........ *A61F 2/30771* (2013.01); *A61F 2/2846* (2013.01); *A61F 2/446* (2013.01); *A61F 2002/30006* (2013.01); *A61F 2002/30583* (2013.01); *A61F 2002/30589* (2013.01); *A61F 2002/30772* (2013.01); *A61F 2002/30851* (2013.01); *A61F 2002/3092* (2013.01)

(58) Field of Classification Search
CPC ........ A61F 2/441; A61F 2/4455; A61F 2/446; A61F 2/4465; A61F 2/447; A61F 2002/4435; A61F 2002/4495
See application file for complete search history.

(56) References Cited

U.S. PATENT DOCUMENTS 8,663,332 B1 * 3/2014 To ......................... A61F 2/4611 623/17.12
9,439,779 B2 9/2016 Zhang et al.
9,456,901 B2 10/2016 Jones et al.
10,772,732 B1 * 9/2020 Miller ................. A61F 2/30771
10,952,866 B2 3/2021 Warren et al.
(Continued)

FOREIGN PATENT DOCUMENTS

CN 101909548 A * 12/2010 ........... A61F 2/3094
CN 102293693 A 12/2011
(Continued)

OTHER PUBLICATIONS

PCT Patent Application PCT/US2024/37307 International Search Report and Written Opinion of the International Searching Authority issued Oct. 25, 2024.

*Primary Examiner* — Eduardo C Robert
(74) *Attorney, Agent, or Firm* — Erise IP, P.A.

(57) ABSTRACT

A porous fusion device configured to aid in fusion of two or more biological tissues. The porous fusion device comprising an exterior frame, an exterior lattice cage within the exterior frame, an interior porous lattice structure, and a material injection port disposed at the exterior frame and projecting into the interior porous lattice structure. The interior porous lattice structure may be characterized by a variable density progression that mimics biological tissues and allows for material dispersal therethrough.

20 Claims, 6 Drawing Sheets

(56) References Cited

U.S. PATENT DOCUMENTS

2006/0276925 A1 12/2006 Lin et al.
2015/0216676 A1* 8/2015 Shulock .................. A61F 2/442
623/17.16
2018/0110624 A1* 4/2018 Arnone ............... A61F 2/30907
2018/0280139 A1 10/2018 Jones et al.
2018/0296350 A1 10/2018 Hamzey et al.
2019/0133783 A1* 5/2019 Unger ................... A61F 2/4455
2019/0151114 A1* 5/2019 Sack ................... A61F 2/30767
2020/0261243 A1 8/2020 Unger et al.
2020/0345506 A1* 11/2020 Ryan ..................... A61F 2/4455
2021/0307921 A1* 10/2021 Newman ................. A61F 2/442
2022/0117753 A1 4/2022 Rucker et al.
2022/0296386 A1* 9/2022 Fang ...................... B33Y 80/00
2022/0324170 A1 10/2022 Reith et al.
2022/0409390 A1* 12/2022 McLean ............. A61B 17/8042
2023/0114676 A1* 4/2023 Harris ................... A61F 2/3094
606/248

FOREIGN PATENT DOCUMENTS

CN 109730814 A 5/2019
CN 109966027 A 7/2019
CN 210250169 U * 4/2020 ............. A61F 2/447
EP 3666231 A1 * 6/2020 ............. A61F 2/447
GB 2561293 A * 10/2018 ............. A61F 2/447

* cited by examiner

POROUS FUSION DEVICE

CROSS-REFERENCE TO RELATED APPLICATIONS

This non-provisional patent application claims priority benefit, with regard to all common subject matter, of U.S. Provisional Patent Application No. 63/528,197, filed Jul. 21, 2023, and entitled "POROUS FUSION DEVICE." The above-identified application is hereby incorporated by reference in its entirety.

TECHNICAL FIELD

Embodiments of the invention relate to a fusion device for use with biological tissues. More specifically, embodiments of the invention relate to a porous fusion device comprising an internal lattice structure.

RELATED ART

Traditional fusion devices do not allow for propagation of fusion material throughout the entirety of the fusion device, including the internal area. This can slow the growth of biological tissues and generally decrease efficacy of the fusion device. Additionally, traditional fusion devices lack structural features that mimic the biological tissues (e.g., bone) they are fusing. Therefore, while biological growth is occurring, the fusion device may behave differently than the tissues being fused. This may cause the tissues to separate from the fusion device and prevent growth and/or fusion from occurring.

SUMMARY

Embodiments of the invention solve the above-mentioned problems by providing a porous fusion device and method of operating thereof. By providing a porous fusion device, materials aiding in fusion of two or more tissues, such as bone graft material, may flow to internal structures of the porous fusion device, thereby increasing the efficacy of tissue fusion. Additionally, the density of porous structures within certain areas of the porous fusion device may be adjusted. These structural adjustments allow the porous fusion device to better mimic the tissue structure of the two or more tissues being fused.

In some embodiments, the techniques described herein relate to a porous fusion device, including: an exterior frame; an exterior lattice cage disposed within the exterior frame; an interior porous lattice structure disposed within the exterior lattice cage; and a material injection port disposed at the exterior lattice cage and projecting into the interior porous lattice structure.

In some embodiments, the techniques described herein relate to a porous fusion device, wherein the material injection port includes a threaded channel, the threaded channel including a first threaded portion and a second threaded portion having a horizontal break therebetween, and wherein the material injection port is configured to interface with an injection tool.

In some embodiments, the techniques described herein relate to a porous fusion device, wherein the horizontal break is configured to disperse applied forces.

In some embodiments, the techniques described herein relate to a porous fusion device, wherein the interior porous lattice structure includes a variable density from the exterior lattice cage to a central-most point of the porous fusion device.

In some embodiments, the techniques described herein relate to a porous fusion device, wherein the variable density includes a gradual decrease in density from the exterior lattice cage to the central-most point of the porous fusion device.

In some embodiments, the techniques described herein relate to a porous fusion device, wherein the exterior lattice cage includes one or more of an octagonal lattice, a heptagonal lattice, a hexagonal lattice, or a pentagonal lattice.

In some embodiments, the techniques described herein relate to a porous fusion device, further including a plurality of material propagation channels disposed through the interior porous lattice structure and the exterior lattice cage.

In some embodiments, the techniques described herein relate to a porous fusion device, further including a backstop disposed opposite of the material injection port, the backstop configured to retain injected material within the porous fusion device.

In some embodiments, the techniques described herein relate to a porous fusion device for fusing two or more tissues, including: an exterior frame; an exterior lattice cage disposed within the exterior frame; an interior porous lattice structure disposed within the exterior lattice cage; a material injection port disposed at the exterior lattice cage and projecting into the interior porous lattice structure; and a plurality of material propagation channels disposed within the interior porous lattice structure and extending to the exterior lattice cage, wherein the interior porous lattice structure is organized by a variable density from the exterior lattice cage to a central-most point of the porous fusion device, wherein the porous fusion device is configured to be backfilled with a material following insertion into a patient.

In some embodiments, the techniques described herein relate to a porous fusion device, wherein the plurality of material propagation channels includes at least one horizontal material propagation channel fluidly coupled to at least one vertical material propagation channel.

In some embodiments, the techniques described herein relate to a porous fusion device, wherein the at least one vertical material propagation channel extends through the exterior frame.

In some embodiments, the techniques described herein relate to a porous fusion device, wherein the material injection port further includes a threaded channel having a first threaded portion and a second threaded portion with a break disposed therebetween.

In some embodiments, the techniques described herein relate to a porous fusion device, wherein the plurality of material propagation channels includes at least one horizontal material propagation channel fluidly coupled to at least one radially extending material propagation channel.

In some embodiments, the techniques described herein relate to a porous fusion device, wherein the plurality of material propagation channels is arranged to direct the material towards the two or more tissues.

In some embodiments, the techniques described herein relate to a method of instructing use of a porous fusion device, including: providing the porous fusion device including: an exterior frame; an exterior lattice cage disposed within the exterior frame; an interior porous lattice structure disposed within the exterior lattice cage; and a material injection port disposed at the exterior lattice cage and projecting into the interior porous lattice structure; instructing attaching a material injection tool to the material injection port of the porous fusion device; instructing inserting the porous fusion device between at least two biological tissues; instructing filling at least part of the porous fusion device with a material via the material injection tool; and instructing disconnecting the material injection tool from the material injection port on the porous fusion device.

In some embodiments, the techniques described herein relate to a method, wherein the material injection port of the porous fusion device further includes a threaded channel including a first threaded portion and a second threaded portion having a break disposed therebetween.

In some embodiments, the techniques described herein relate to a method, wherein instructing filling at least part of the porous fusion device with the material occurs prior to instructing inserting the porous fusion device between the at least two biological tissues.

In some embodiments, the techniques described herein relate to a method, wherein the material injected into the porous fusion device is bone graft material.

In some embodiments, the techniques described herein relate to a method, wherein the interior porous lattice structure of the porous fusion device is organized by a variable density from the exterior lattice cage of the porous fusion device to a central-most point of the porous fusion device.

In some embodiments, the techniques described herein relate to a method, wherein the porous fusion device further includes a backstop disposed opposite of the material injection port and configured to retain the material injected into the porous fusion device.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1:
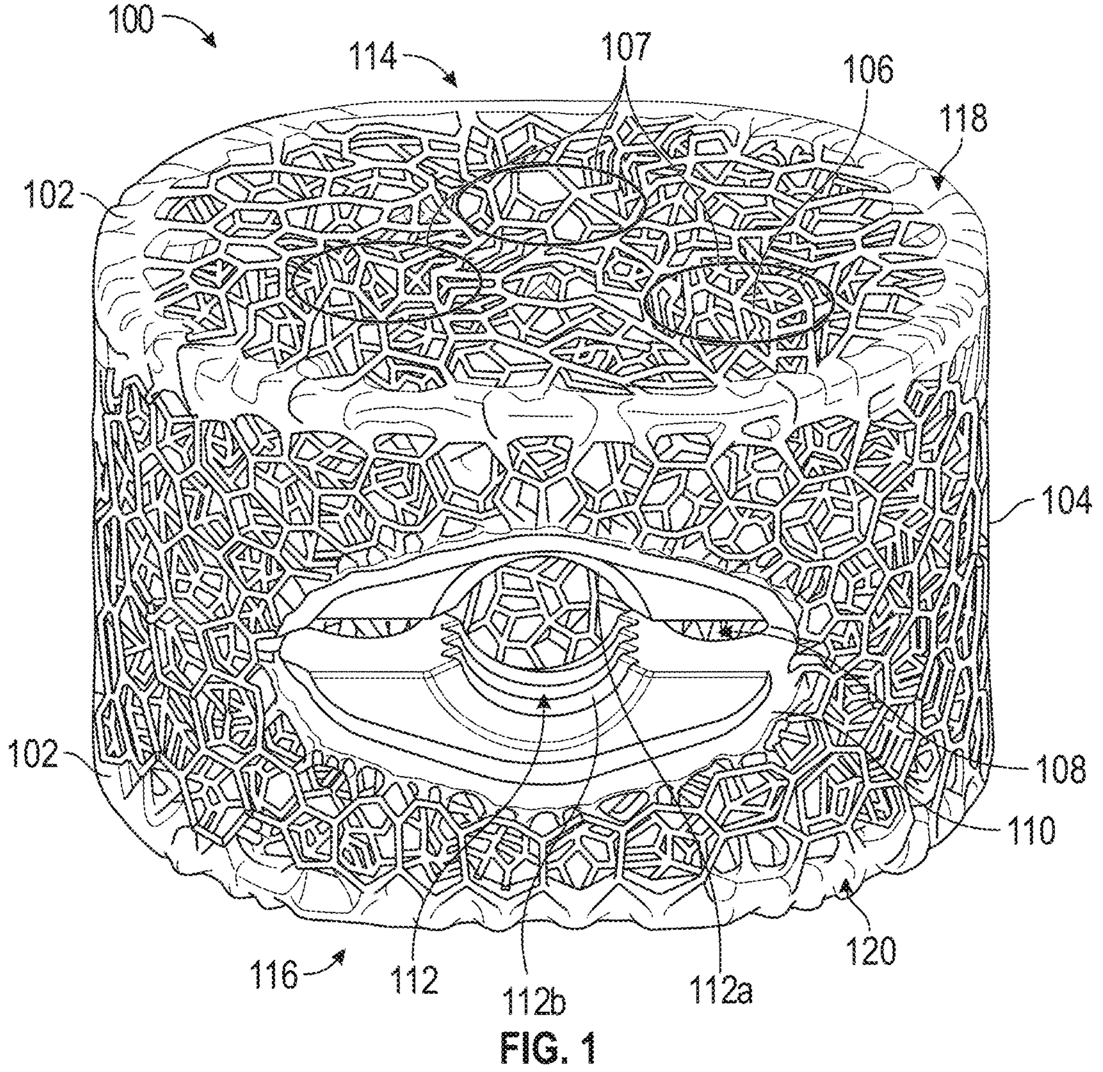
FIG. 1 illustrates a porous fusion device, in some embodiments.

The drawing figures do not limit the invention to the specific embodiments disclosed and described herein. The drawings are not necessarily to scale, emphasis instead being placed upon clearly illustrating the principles of the invention.

DETAILED DESCRIPTION

The subject matter of the invention is described in detail below to meet statutory requirements; however, the description itself is not intended to limit the scope of claims. Rather, the claimed subject matter might be embodied in other ways to include different steps or combinations of steps similar to the ones described in this document, in conjunction with other present or future technologies. Minor variations from the description below will be understood by one skilled in the art and are intended to be captured within the scope of the claimed invention. Terms should not be interpreted as implying any particular ordering of various steps described unless the order of individual steps is explicitly described.

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Turning first to FIG. 1, porous fusion device 100 is shown. In some embodiments, porous fusion device 100 may comprise exterior frame 102, exterior lattice cage 104, interior porous lattice structure 106, secondary propagation channels 107, break 108, material injection port 110, connection port 112, superior region 114, inferior region 116, first horizontal frame 118, and second horizontal frame 120. In some embodiments, exterior frame 102 provides structural support to the tissues being fused by porous fusion device 100. In some embodiments, exterior frame 102 provides structural support to porous fusion device 100. In some embodiments, exterior frame 102 may comprise two horizontal frames (e.g., first horizontal frame 118 and second horizontal frame 120) spanned by exterior lattice cage 104. While two horizontal frames are depicted for exterior frame 102, any number of frames in any orientation may be used for exterior frame 102. In some embodiments, interior porous lattice structure 106 may fill the volume within exterior frame 102.

In some embodiments, exterior frame 102 may be arranged according to a first plane. Below, certain aspects and/or components of porous fusion device 100 may be described using directional terms (e.g., horizontal, vertical, superior, inferior, etc.). It is noted that these terms are merely for descriptive purposes with respect to the Figs., and that any aspect and/or component of porous fusion device 100 may be in any direction depending on the orientation of porous fusion device 100 prior to and following implantation. In some embodiments, exterior frame 102 may comprise first horizontal frame 118 associated with superior region 114 of porous fusion device 100 and second horizontal frame 120 associated with inferior region 116 of porous fusion device 100. In some embodiments, exterior lattice cage 104 extends between first horizontal frame 118 and second horizontal frame 120. In some embodiments, interior porous lattice structure 106 may occupy at least a portion of the space between superior region 114 and inferior region 116. In some embodiments, first horizontal frame 118 and second horizontal frame 120 may be parallel or substantially parallel to each other. In some embodiments, first horizontal frame 118 and second horizontal frame 120 may be at any angle other than parallel with respect to one another.

In some embodiments, secondary propagation channels 107 may extend through interior porous lattice structure 106 and secondary propagation channels 107 may be arranged partially or fully between first horizontal frame 118 and second horizontal frame 120. In some embodiments, material injection port 110 may be disposed at exterior frame 102 between first horizontal frame 118 and second horizontal frame 120. For example, in some embodiments, material injection port 110 may be positioned at an equidistance point between first horizontal frame 118 and second horizontal frame 120 along exterior frame 102. In some embodiments, break 108 may be oriented roughly parallel to one or both of first horizontal frame 118 or second horizontal frame 120. In some embodiments, horizontal break 108 may be oriented at an angle other than parallel with respect to one or both of first horizontal frame 118 or second horizontal frame 120.

In some embodiments, material injection port 110 may comprise an elongated portion (e.g., an oblong, oval shape), as illustrated. In some embodiments, the elongated portion of material injection port 110 may extend roughly parallel to first horizontal frame 118 and/or second horizontal frame 120, as illustrated. Alternatively, in some embodiments, the elongated portion of material injection port 110 may extend at an angle other than parallel with respect to first horizontal frame 118 and/or second horizontal frame 120. In embodiments in which material injection port 110 includes an elongated portion, such an arrangement may aid in dispersion of applied forces (e.g., torsional forces) exerted on porous fusion device 100, such as connection of an insertion device. Such dispersion of forces may prevent breaking or otherwise damaging porous fusion device 100 during various steps of implantation of porous fusion device 100. In some embodiments, material injection port 110 may comprise any other shape, such as circular, square, hexagonal, etc.

In some embodiments, exterior lattice cage 104 may be an octagonal lattice, a heptagonal lattice, a hexagonal lattice, a pentagonal lattice, a square lattice, or any form of lattice structure. In some embodiments, exterior lattice cage 104 may be a horizontal and vertical grid. In some embodiments, exterior lattice cage 104 may be a diagonal grid. In some embodiments, exterior lattice cage 104 may cover the sides of porous fusion device 100. In some embodiments, exterior lattice cage 104 may not cover some or all of inferior region 116 of porous fusion device 100.

In some embodiments, material injection port 110 is incorporated into exterior frame 102. In some embodiments, material injection port 110 may project through exterior lattice cage 104 and into interior porous lattice structure 106. In some embodiments, material injection port 110 includes connection port 112. In some embodiments, connection port 112 may be configured to interface with a plurality of tools such as: a bolt, a material injection tool, a mounting device, an insertion and/or removal tool, a robotic appendage, a power drill, a threaded insert, or any other compatible tool. Material injection port 110 may further comprise break 108. Similar to the shape of material injection port 110 described above, in some embodiments, break 108 may prevent damage (e.g., torsional damage) to porous fusion device 100 during insertion with any of the aforementioned tools. In some embodiments, break 108 may be configured to prevent damage to porous fusion device 100 by reducing the stiffness of connection port 112. In some embodiments, break 108 may separate connection port 112 into first threaded portion 112*a* and second threaded portion 112*b*.

In some embodiments, connection port 112 may have no threads and instead comprise a mechanical fastener to attach to an injection tool. In some embodiments, the mechanical fastener is a rivet, a clamp, a latch, a conical anchor, an expansion anchor, or any other form of mechanical fastener. In some embodiments, the injection tool is attached to porous fusion device 100 using adhesive. In some embodiments, the adhesive may be heat-dissolving adhesive, bio-adaptable adhesive, bio-consumable adhesive, any combination of these, or any other form of adhesive.

Figure 3:
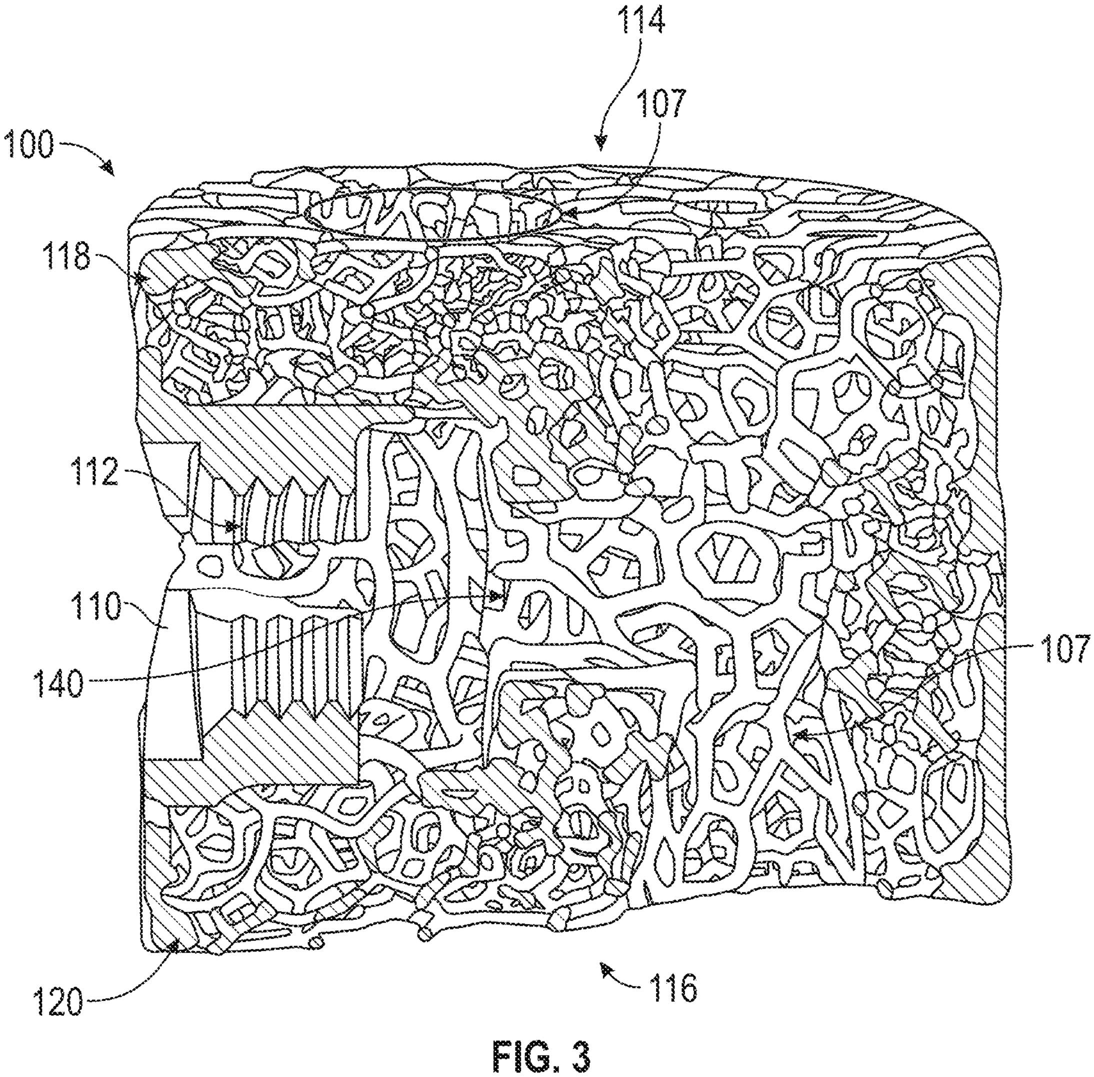
FIG. 3 illustrates a cross-sectional view of a porous fusion device, in some embodiments.

In some embodiments, porous fusion device 100 comprises secondary propagation channels 107 disposed through or substantially through exterior lattice cage 104 and the interior porous lattice structure 106. In some embodiments, secondary propagation channels 107 aid in the propagation of a material throughout the porous fusion device 100. In some embodiments, secondary propagation channels 107 provide a path for bio-structure growth. In some embodiments, porous fusion device 100 may further comprise at least one primary propagation channel (e.g., primary propagation channel 140 as depicted in FIG. 3) configured to fluidly couple material injection port 110 and secondary propagation channels 107 to allow propagation of material towards secondary propagation channels 107.

In some embodiments, exterior frame 102 includes structural supports (not illustrated here) extending from superior region 114 of porous fusion device 100 to inferior region 116 of porous fusion device 100. For example, structures having a higher density than exterior lattice cage 104 may span the vertical length of porous fusion device 100 to improve structural integrity of porous fusion device 100 under compressive forces. In some embodiments, exterior lattice cage 104 may be incorporated into the structural supports and span any gaps between them. In some embodiments, the structural supports are temporary and dissolve or otherwise disintegrate following implantation of porous fusion device 100.

In some embodiments, interior porous lattice structure 106 and exterior lattice cage 104 may be configured to mimic bone material. As described below in relation to FIGS. 4A-4D, in some embodiments, interior porous lattice structure 106 may be configured to have a stronger exterior and a weaker interior structure. In some embodiments, interior porous lattice structure 106 may be configured to mimic bone material such that interior porous lattice structure 106 may have a higher density exterior that gradually progresses to a lower density interior. In some embodiments, exterior lattice cage 104 may be configured to have a higher density than interior porous lattice structure 106 such that porous fusion device 100 mimics bone material by providing a higher density and strength exterior and a lower density and strength interior.

Figure 2:
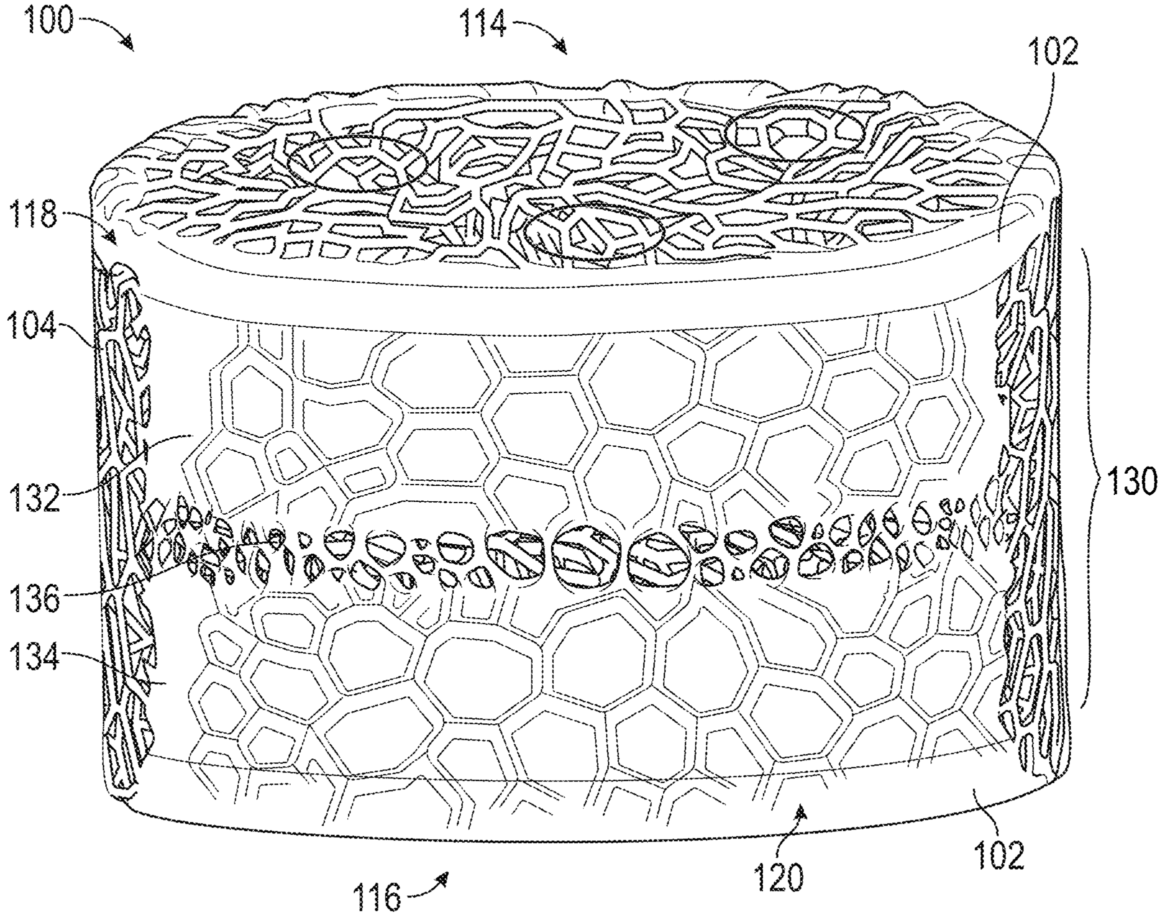
FIG. 2 illustrates a rear view of a porous fusion device, in some embodiments.

In FIG. 2, an exemplary rear view of porous fusion device 100 is depicted. In some embodiments, porous fusion device 100 includes backstop 130, which may be incorporated into exterior lattice cage 104. In some embodiments, backstop 130 includes first backstop 132, second backstop 134, and spanning channel 136 therebetween. In some embodiments, backstop 130 extends a distance from one or both of first horizontal frame 118 or second horizontal frame 120. For example, as depicted, first backstop 132 extends a distance away from first horizontal frame 118 and second backstop 134 extends a distance away from second horizontal frame 120. In some embodiments, backstop 130 is configured to redirect the propagation of material injected into porous fusion device 100. For example, backstop 130 may redirect injected material back towards the interior of porous fusion device 100, such as within interior porous lattice structure 106. In some embodiments, backstop 130 provides additional structural support to porous fusion device 100. In some embodiments, backstop 130 further comprises spanning channel 136. As illustrated, exterior lattice cage 104 may extend through spanning channel 136. In some embodiments, spanning channel 136 may be uniform with first backstop 132 and second backstop 134, forming a unitary backstop comprising first backstop 132, second backstop 134, and spanning channel 136.

In some embodiments, spanning channel 136 may be configured to absorb compressive forces exerted on porous fusion device 100. For example, in embodiments that utilize porous fusion device 100 as a vertebral fusion device, the two adjacent vertebrae will exert compressive forces on porous fusion device 100 at superior region 114 and inferior region 116. Accordingly, if these compressive forces exceed a threshold, spanning channel 136 may provide a flexible, absorbing region which is less rigid than surrounding portions of porous fusion device 100 (e.g., superior region 114 and inferior region 116). As spanning channel 136 comprises a less rigid structure, spanning channel 136 may compress slightly or fully during exertion of the compressive forces. In some embodiments, spanning channel 136 may be configured to return to the original structure formation upon relief of the compressive forces. In this manner, spanning channel 136 may allow porous fusion device 100 to more closely mimic the modulus of bone compared to a fully rigid fusion device. In some embodiments, spanning channel 136 may alternatively comprise a rigid structure that resists compressive forces exerted by spanning bony structures (e.g., two adjacent vertebrae).

In some embodiments, backstop 130 may partially or fully enclose exterior lattice cage 104. For example, backstop 130 may replace or otherwise cover the entirety of exterior lattice cage 104, thereby fully enclosing porous fusion device 100. In some embodiments, backstop 130 may be configured to prevent injected material, such as bone graft material, from exiting porous fusion device 100. In some embodiments, backstop 130 may cover the vertical portions of exterior lattice cage 104 while not covering the non-vertical portions. For example, in some embodiments, backstop 130 may not cover superior region 114 or inferior region 116 of porous fusion device 100, thereby allowing material to propagate out of porous fusion device 100 through superior region 114 and/or inferior region 116 and towards adjacent bones.

In FIG. 3, exemplary embodiments of porous fusion device 100 are depicted in a cross-sectional side view. Porous fusion device 100 may include a primary propagation channel 140, as mentioned above. Primary propagation channel 140 may be fluidly connected with secondary propagation channels 107. Primary propagation channel 140 may extend from material injection port 110 to allow propagation of material through primary propagation channel 140 towards secondary propagation channels 107. In some embodiments, primary propagation channel 140 may be a plurality of propagation channels. In some embodiments, primary propagation channel 140 and secondary propagation channels 107 combine to form a propagation channel network. In some embodiments, primary propagation channel 140 may comprise a low-density lattice structure therein to allow propagation of material through the low-density lattice structure of primary propagation channel 140 towards secondary propagation channels 107.

In some embodiments, at least one primary propagation channel 140 may be oriented parallel to first horizontal frame 118 or second horizontal frame 120, as described with respect to FIG. 1. In some embodiments, at least one secondary propagation channel 107 may be oriented roughly perpendicular to first horizontal frame 118 or second horizontal frame 120. In some embodiments, at least one secondary propagation channel 107 may be oriented perpendicular to first horizontal frame 118 or second horizontal frame 120. In some embodiments, at least one secondary propagation channel 107 may be oriented perpendicular to at least one primary propagation channel 140.

In some embodiments, the propagation channel network may be configured to extend throughout a majority of porous fusion device 100. The propagation channel network may be configured to slow the propagation of material as the material propagates towards exterior lattice cage 104. For example, secondary propagation channels 107 may become narrower as they extend outwardly from primary propagation channel 140. In some embodiments, second propagation channels 107 may comprise a low-density lattice structure therein to slow the propagation of material outward towards exterior lattice cage 104. In some embodiments, the propagation channel network may provide an unimpeded path (e.g., maintain the same width and/or radius) for propagation of material towards exterior lattice cage 104. In some embodiments, the density of interior porous lattice structure 106 may prevent material flow therethrough, such that injected material only flows through the propagation network (e.g., primary propagation channel 140 and secondary propagation channels 107). The propagation channel network may be enclosed by exterior lattice cage 104 such that the propagation channel network forms a plurality of horizontal, vertical, and/or any other orientation of propagation channels directed towards exterior lattice cage 104.

While secondary propagation channels 107 are depicted as extending roughly perpendicular from primary propagation channel 140, in some embodiments, secondary propagation channels 107 may extend at a different angle from primary propagation channel 140. For example, in some embodiments, secondary propagation channels 107 may extend radially from primary propagation channel 140. In some embodiments, secondary propagation channels 107 may extend parallel to primary propagation channel 140, but may change directions towards exterior lattice cage 104. Such directional change and specificity of material propagation is advantageous for targeted distribution of the injected material towards specific areas of the biological tissue. For example, radially directed secondary propagation channels 107 may distribute more injected material towards the exterior of the adjacent bones. Such distribution may aid in fusion and/or healing of these exterior areas of the adjacent bone. In these embodiments, a porous fusion device 100 having specifically directed secondary propagation channels 107 may be chosen based on the biological tissue being fused and/or healed. In some embodiments, the material propagation network aids in propagation of material injected into material injection port 110 throughout porous fusion device 100, such as through interior porous lattice structure 106.

In some embodiments, secondary propagation channels 107 may be fluidly coupled to primary propagation channel 140. In some embodiments, connection port 112 may be fluidly coupled to primary propagation channel 140. In some embodiments, secondary propagation channels 107, primary propagation channel 140, and connection port 112 may be fluidly coupled together to provide a material propagation network within porous fusion device 100. In some embodiments, connection port 112 may be fluidly coupled to secondary propagation channels 107. In some embodiments, secondary propagation channels 107 may be absent and connection port 112 may be fluidly coupled to primary propagation channel 140. In some embodiments, primary propagation channel 140 may be absent and connection port 112 may be fluidly coupled to secondary propagation channels 107.

In some embodiments, the material propagation network may be arranged within interior porous lattice structure 106 such that the material propagation network may be disposed between first horizontal frame 118 and second horizontal frame 120. In some embodiments, the material propagation network may comprise a combination of at least one primary propagation channel 140 and at least one secondary propagation channel 107 such that material may propagate through porous fusion device 100 in a multitude of directions (e.g., horizontal and vertical directions). In some embodiments, the material propagation network may be disposed through first horizontal frame 118 and second horizontal frame 120 such that material propagates against a first and second tissue contacting superior region 114 and inferior region 116, respectively.

In some embodiments, two or more tissues being fused are oriented with respect to first horizontal frame 118 and second horizontal frame 120. In some embodiments, superior region 114 and inferior region 116 contact the tissues to be fused in accordance with first horizontal frame 118 and second horizontal frame 120 such that material may propagate out of porous fusion device 100 and contact the two or more tissues to be fused.

Figures 4A, 4B, 4C:
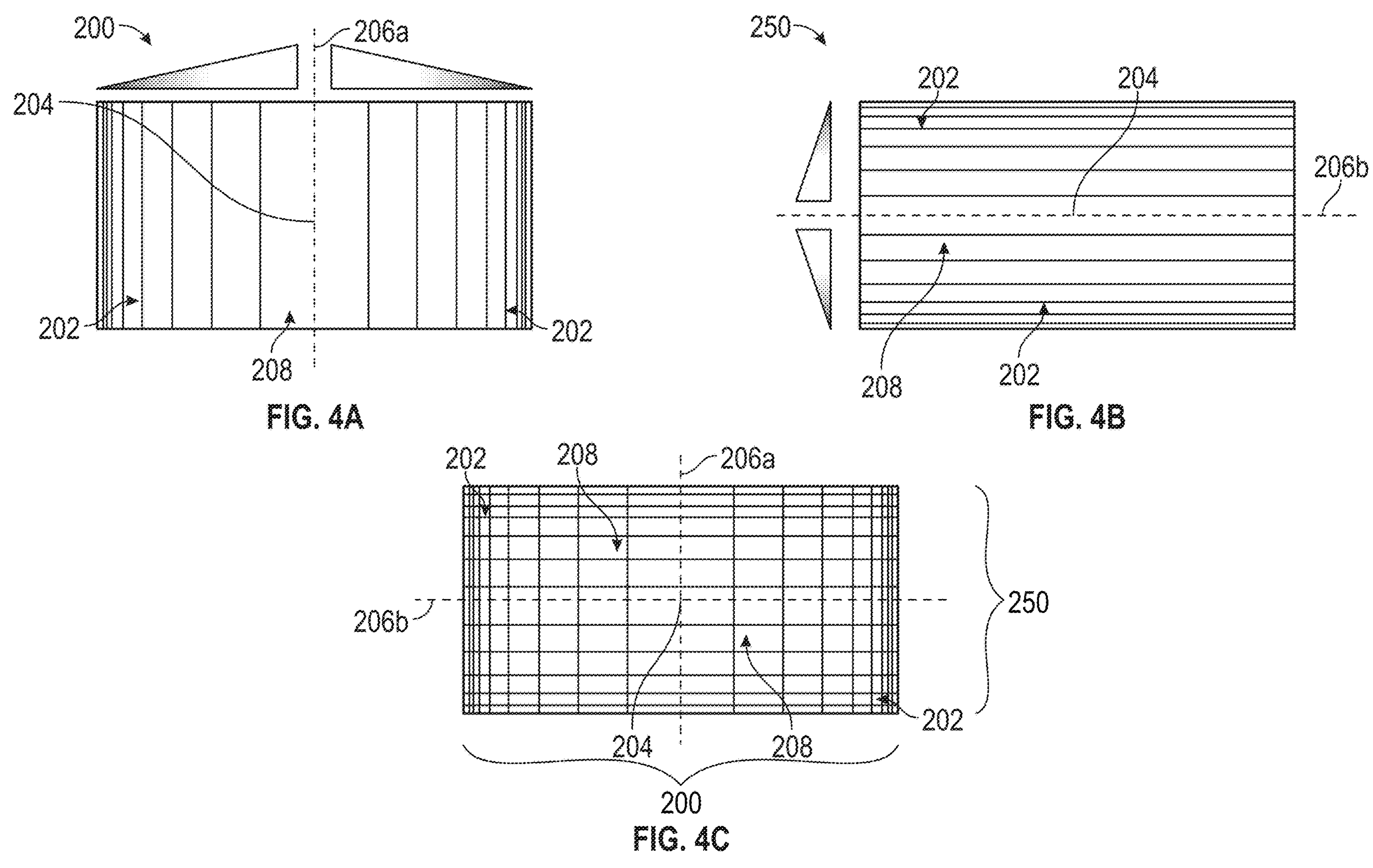
FIG. 4A illustrates an exemplary embodiment of a variable density progression in a first direction.
FIG. 4B illustrates an exemplary embodiment of a variable density progression in a second direction.
FIG. 4C illustrates an exemplary embodiment of a variable density progression in a first and second direction.

Turning now to FIG. 4A, an illustration of variable density progression 200 is shown for exemplary purposes. In some embodiments, interior porous lattice structure 106 may be organized as illustrated variable density progression 200. In some embodiments, the density of interior porous lattice structure 106 is variable throughout porous fusion device 100. Varying density of interior porous lattice structure 106 may alter the rate of flow of a material therethrough. To aid in explanation, FIGS. 4A and 4B illustrate variable density progression 200 and 250, respectively. In some embodiments, variable density progression 200 varies density between a region of high density 202 and a region of low density 208. In some embodiments, variable density progression 200 varies density between region of high density 202 to central-most point 204 defining the central point of the depicted vertical plane 206*a*. In some embodiments, region of high density 202 may be exterior lattice cage 104. In some embodiments, central-most point 204 may be disposed within the center of porous fusion device 100.

Related to variable density progression 200 and 250, in some embodiments, the structure of interior porous lattice structure 106 is of an entropic nature. The porous structures defining interior porous lattice structure 106 may be random such that the porous structures are heterogeneous (e.g., varying in size, shape, etc.). Accordingly, the entropic nature of the porous structures defining interior porous lattice structure 106 may be organized in a manner so as to define the variable densities (e.g., variable density progression 200 and 250) throughout interior porous lattice structure 106. Similarly, in some embodiments, the structure of exterior lattice cage 104 is of an entropic nature similar to that described above.

In FIG. 4B, an illustration of variable density progression 250 is shown for exemplary purposes. In some embodiments, interior porous lattice structure 106 may be organized as illustrated variable density progression 250. In some embodiments, variable density progression 200 follows a horizontal progression through porous fusion device 100 as moving away from depicted vertical plane 206*a*. In some embodiments, variable density progression 250 follows a vertical progression through porous fusion device 100 as moving away from depicted horizontal plane 206*b*. In some embodiments, variable density progression 200 and variable density progression 250 follow a horizontal and a vertical progression, respectively, through porous fusion device 100. In some embodiments, variable density progression 200 and variable density progression 250 may be reversed and follow an opposite progression from high density to low density as moving away from central-most point 204.

In some embodiments, interior porous lattice structure 106 is organized by one or both of variable density progression 200 and variable density progression 250. For example, variable density progression 200 and 250 may extend radially outward from central-most point 204 (e.g., as illustrated in FIG. 4C). In such an embodiment, central-most point 204 may be centrally located within porous fusion device 100. In some embodiments, interior porous lattice structure 106, as organized by variable density progression 200 and 250, may decrease in density as interior porous lattice structure 106 approaches central-most point 204. In some embodiments, interior porous lattice structure 106, as organized by variable density progression 200 and 250, may increase in density as interior porous lattice structure 106 approaches exterior lattice cage 104.

In some embodiments, the gradual progression of density between region of low density 208 and region of high density 202 may be characterized by variable density progression 200 and 250. While not depicted, in some embodiments, the gradual progression of density between region of low density 208 and region of high density 202 may be characterized by an inverse of variable density progression 200 and 250. For example, the density of interior porous lattice structure 106 may decrease as transitioning away from central-most point 204.

Figure 4D:
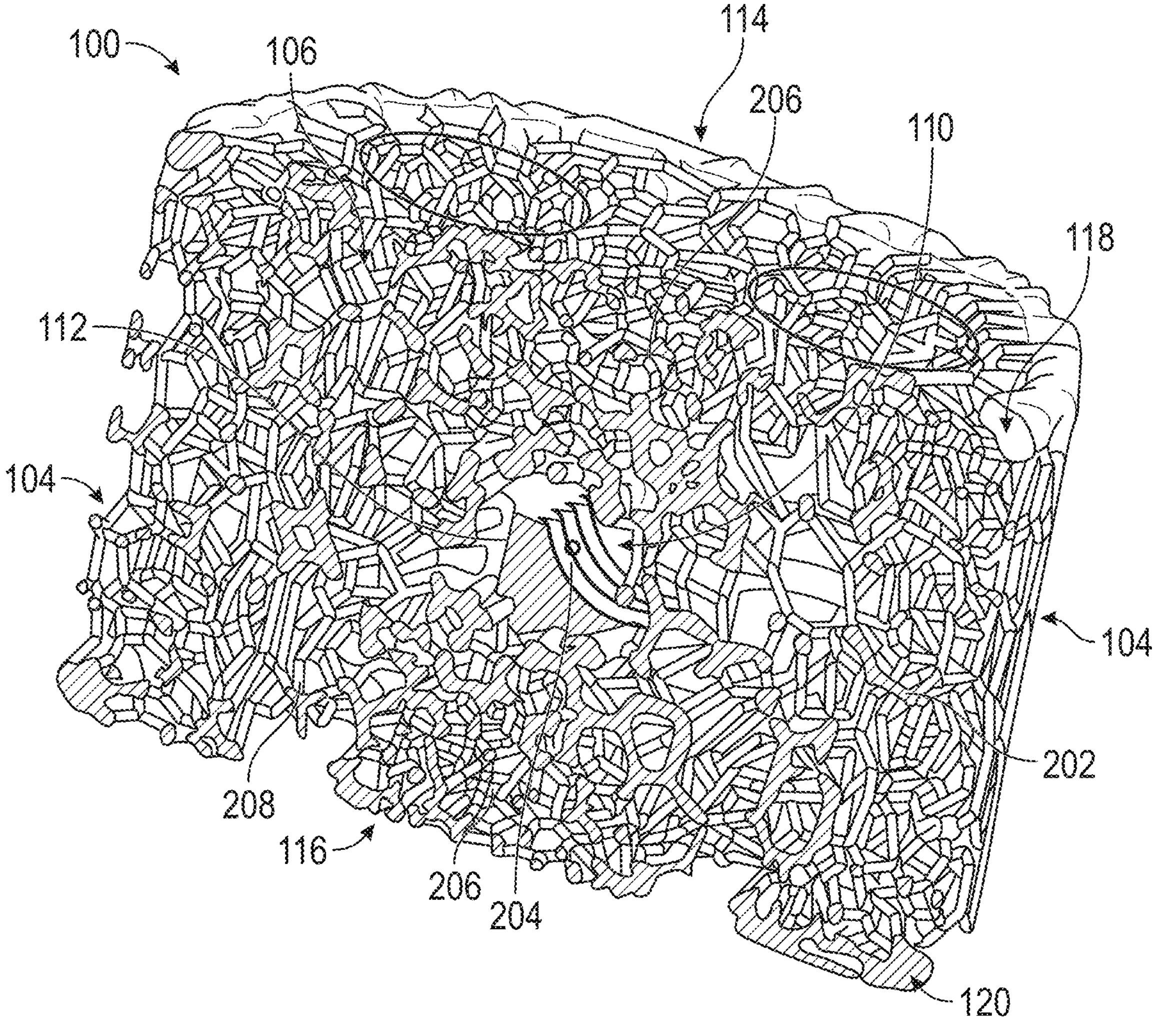
FIG. 4D illustrates a cross-sectional view of a porous fusion device as organized by a variable density progression.

In FIG. 4C, an exemplary combination of variable density progression 200 and variable density progression 250 is illustrated. Porous fusion device 100 may comprise a plurality of regions of varying density as described above in relation to FIG. 4A and FIG. 4B. In some embodiments, region of high density 202 may be disposed near the exterior of porous fusion device 100. For example, region of high density 202 is disposed near exterior lattice cage 104 (as depicted in FIG. 4D). Porous fusion device 100 may further comprise regions of low density such as region of low density 208. In some embodiments, region of low density 208 is disposed near central-most point 204. In some embodiments, the lowest point of density may be characterized by central-most point 204 which may be centrally located within porous fusion device 100. In some embodiments, interior porous lattice structure 106 may be organized by variable density progression 200 such that the structure of interior porous lattice structure 106 gradually progresses from low density to high density as moving away from central-most point 204.

While not depicted herein, in some embodiments, exterior lattice cage 104 may vary in density along one or more of the horizontal, vertical, or radial directions. Such changes in the density of exterior lattice cage 104 may aid in directing the extrusion of material externally to porous fusion device 100. Additionally, or alternatively, as discussed above, backstop 130 may cover portions of exterior lattice cage 104 to prevent material extrusion from exterior lattice cage 104 in certain areas while allowing material extrusion in other areas not covered by backstop 130.

In some embodiments, interior porous lattice structure 106 may extend radially outward from central-most point 204. In such embodiments, interior porous lattice structure 106 may be characterized by at least one variable density progression (e.g., variable density progression 200 and/or variable density progression 250) that mimics biological tissues and/or allows for material dispersal therethrough.

While interior porous lattice structure 106 is depicted and discussed as comprising variable density throughout porous fusion device 100, in some embodiments, the density of interior porous lattice structure 106 may be substantially similar throughout porous fusion device 100.

In FIG. 4D, an embodiment of porous fusion device 100 is illustrated as organized by variable density progression 200 and 250. In some embodiments, region of high density 202 may be disposed near exterior lattice cage 104. In some embodiments, central-most point 204 may be disposed within connection port 112. In some embodiments, region of low density 208 may be disposed near central-most point 204. In some embodiments, at least part of interior porous lattice structure 106 may be organized by region of high density 202 and region of low density 208.

Figure 5:
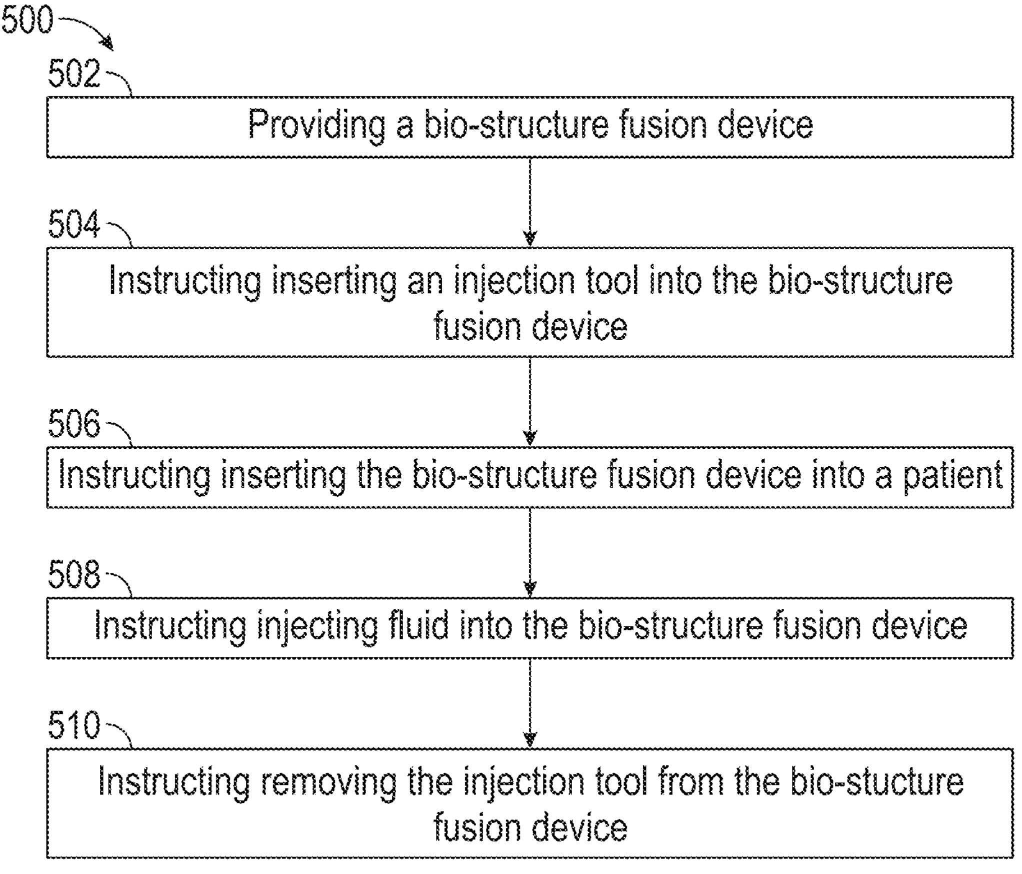
FIG. 5 is a flowchart illustrating an exemplary method for instructing use of a porous fusion device.

In FIG. 5, an exemplary method 500 for instructing operation of a porous fusion device is depicted. At step 502, a bio-structure fusion device is provided, such as a porous fusion device. For example, porous fusion device 100 may be provided. In some embodiments, porous fusion device 100 may further comprise additional features not present in this disclosure.

At step 504, instructions for inserting an injection tool into a bio-structure fusion device via a material injection port are provided. For example, instructions for inserting an injection tool (not depicted) into porous fusion device 100 via material injection port 110 are provided. The injection tool may be configured to interface with connection port 112. In some embodiments, material may be injected into porous fusion device 100 using the injection tool during step 502. In some embodiments, porous fusion device 100 may be pre-filled before step 502. Porous fusion device 100 may be transiently attached to the injection tool such that porous fusion device 100 may be inserted and implanted into a patient.

At step 506, instructions for inserting the bio-structure fusion device (e.g., porous fusion device 100) into a patient may be provided. In some embodiments, instructions for inserting porous fusion device 100 between two or more tissues (e.g., bones) may be provided, such that porous fusion device 100 facilitates growth of the two or more tissues in and around porous fusion device 100. In some embodiments, porous fusion device 100 may not be inserted between two or more tissues and instead may be attached to a single tissue. For example, porous fusion device 100 may extend a single tissue by facilitating growth of the tissue at and from the attachment site.

At step 508, instructions for injecting material (e.g., fluid) into the bio-structure fusion device may be provided. For example, in some embodiments, instructions for backfilling porous fusion device 100 via an injection tool are provided. In some embodiments, the material may be bone graft material, bone growth facilitating chemicals, bio-foam, bone marrow, synthetic bone graft material, or any other tissue growth facilitating material. In some embodiments, the material may have a viscosity higher than that of bone graft material such that the material may propagate through a low-density portion (e.g., region of low density 208) of porous fusion device 100. In some embodiments, the material may have a viscosity lower than that of bone-graft material such that the material may propagate through a high density portion (e.g., region of high density 202) of porous fusion device 100. In some embodiments, the structure of interior porous lattice structure 106 may correspond with the viscosity of material to be injected into porous fusion device 100. For example, a high-viscosity material may be used with a low density interior porous lattice structure 106. Alternatively, a low-viscosity material may be used with a high density interior porous lattice structure 106. In some embodiments, the medical professional may be instructed to adjust the viscosity of the material based on the density or variable density of interior porous lattice structure 106. Alternatively, in some embodiments, the material of the correct viscosity is provided to the medical professional along with the porous fusion device 100 having the corresponding density of interior porous lattice structure 106.

As discussed above, the material may be injected into porous fusion device 100 by an injection tool. In some embodiments, step 508 may be optional as porous fusion device 100 may be pre-filled with material and provided to the medical professional. In such an embodiment, porous fusion device 100 may be injected with material as part of the manufacturing process and provided to the medical professional pre-filled with the material.

At step 510, instructions for disconnecting the injection tool from the bio-structure fusion device (e.g., porous fusion device 100) and removing the injection tool from the patient are provided. The injection tool may be reinserted after step 510 to add additional material. The additional material may be of the same or differing composition as the initially injected/placed material. In some embodiments, further steps are included in method 500 such as; placing a porous fusion device cover on porous fusion device 100, inserting a secondary fusion device or other component to fill the cavity defined by material injection port 110, injecting a secondary material into porous fusion device 100 to cause a chemical reaction that facilitates tissue fusion and/or growth, and removing and/or rasping any amount of tissue from the patient prior to inserting porous fusion device 100.

Features described above as well as those claimed below may be combined in various ways without departing from the scope hereof. The following examples illustrates some possible, non-limiting combinations:

(A1) A porous fusion device, comprising: an exterior frame; an exterior lattice cage disposed within the exterior frame; an interior porous lattice structure disposed within the exterior lattice cage; and a material injection port disposed at the exterior lattice cage and projecting into the interior porous lattice structure.

(A2) For the porous fusion device denoted as (A1), wherein the material injection port comprises a threaded channel, the threaded channel comprising a first threaded portion and a second threaded portion having a horizontal break therebetween, and wherein the material injection port is configured to interface with an injection tool.

(A3) For the porous fusion device denoted as (A1) or (A2), wherein the horizontal break is configured to disperse applied forces.

(A4) For the porous fusion device denoted as (A1) through (A3), wherein the interior porous lattice structure comprises a variable density from the exterior lattice cage to a central-most point of the porous fusion device.

(A5) For the porous fusion device denoted as (A1) through (A4), wherein the variable density comprises a gradual decrease in density from the exterior lattice cage to the central-most point of the porous fusion device.

(A6) For the porous fusion device denoted as (A1) through (A5), wherein the exterior lattice cage comprises one or more of an octagonal lattice, a heptagonal lattice, a hexagonal lattice, or a pentagonal lattice.

(A7) For the porous fusion device denoted as (A1) through (A6), further comprising a plurality of material propagation channels disposed through the interior porous lattice structure and the exterior lattice cage.

(A8) For the porous fusion device denoted as (A1) through (A7), further comprising a backstop disposed opposite of the material injection port, the backstop configured to retain injected material within the porous fusion device.

(B1) A porous fusion device for fusing two or more tissues, comprising: an exterior frame; an exterior lattice cage disposed within the exterior frame; an interior porous lattice structure disposed within the exterior lattice cage; a material injection port disposed at the exterior lattice cage and projecting into the interior porous lattice structure; and a plurality of material propagation channels disposed within the interior porous lattice structure and extending to the exterior lattice cage, wherein the interior porous lattice structure is organized by a variable density from the exterior lattice cage to a central-most point of the porous fusion device, wherein the porous fusion device is configured to be backfilled with a material following insertion into a patient.

(B2) For the porous fusion device denoted as (B1), wherein the plurality of material propagation channels comprises at least one horizontal material propagation channel fluidly coupled to at least one vertical material propagation channel.

(B3) For the porous fusion device denoted as (B1) or (B2), wherein the at least one vertical material propagation channel extends through the exterior frame.

(B4) For the porous fusion device denoted as (B1) through (B3), wherein the material injection port further comprises a threaded channel having a first threaded portion and a second threaded portion with a break disposed therebetween.

(B5) For the porous fusion device denoted as (B1) through (B4), wherein the plurality of material propagation channels comprises at least one horizontal material propagation channel fluidly coupled to at least one radially extending material propagation channel.

(B6) For the porous fusion device denoted as (B1) through (B5), wherein the plurality of material propagation channels is arranged to direct the material towards the two or more tissues.

(C1) A method of instructing use of a porous fusion device, comprising: providing the porous fusion device comprising: an exterior frame; an exterior lattice cage disposed within the exterior frame; an interior porous lattice structure disposed within the exterior lattice cage; and a material injection port disposed at the exterior lattice cage and projecting into the interior porous lattice structure; instructing attaching a material injection tool to the material injection port of the porous fusion device; instructing inserting the porous fusion device between at least two biological tissues; instructing filling at least part of the porous fusion device with a material via the material injection tool; and instructing disconnecting the material injection tool from the material injection port on the porous fusion device.

(C2) For the method denoted as (C1), wherein the material injection port of the porous fusion device further comprises a threaded channel comprising a first threaded portion and a second threaded portion having a break disposed therebetween.

(C3) For the method denoted as (C1) or (C2), wherein instructing filling at least part of the porous fusion device with the material occurs prior to instructing inserting the porous fusion device between the at least two biological tissues.

(C4) For the method denoted as (C1) through (C3), wherein the material injected into the porous fusion device is bone graft material.

(C5) For the method denoted as (C1) through (C4), wherein the interior porous lattice structure of the porous fusion device is organized by a variable density from the exterior lattice cage of the porous fusion device to a central-most point of the porous fusion device.

(C6) For the method denoted as (C1) through (C5), wherein the porous fusion device further comprises a backstop disposed opposite of the material injection port and configured to retain the material injected into the porous fusion device.

Many different arrangements of the various components depicted, as well as components not shown, are possible without departing from the scope of the claims below. Embodiments of the present disclosure have been described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims. Although the present disclosure has been described with reference to the embodiments illustrated in the attached drawing figures, it is noted that equivalents may be employed, and substitutions made herein, without departing from the scope of the present disclosure as recited in the claims.

The invention claimed is:

1. A porous fusion device, comprising:

an exterior frame;

an exterior lattice cage disposed within the exterior frame;

an interior porous lattice structure disposed within the exterior lattice cage, wherein the interior porous lattice structure comprises a gradual decrease in density from the exterior lattice cage to a central-most point of the porous fusion device; and a material injection port disposed at the exterior lattice cage and projecting into the interior porous lattice structure.

2. The porous fusion device of claim 1, wherein the material injection port comprises a threaded channel, the threaded channel comprising a first threaded portion and a second threaded portion having a horizontal break therebetween, and wherein the material injection port is configured to interface with an injection tool.

3. The porous fusion device of claim 2, wherein the horizontal break is configured to disperse applied forces.

4. The porous fusion device of claim 1, wherein the exterior lattice cage comprises one or more of an octagonal lattice, a heptagonal lattice, a hexagonal lattice, or a pentagonal lattice.

5. The porous fusion device of claim 1, further comprising a plurality of material propagation channels disposed through the interior porous lattice structure and the exterior lattice cage.

6. The porous fusion device of claim 1, further comprising a backstop disposed opposite of the material injection port, the backstop configured to retain injected material within the porous fusion device.

7. The porous fusion device of claim 6, wherein the backstop comprises a spanning channel disposed between a first portion of the backstop and a second portion of the backstop, the spanning channel configured to absorb compressive forces exerted on the porous fusion device.

8. A porous fusion device for fusing two or more tissues, comprising:

an exterior frame;

an exterior lattice cage disposed within the exterior frame;

an interior porous lattice structure disposed within the exterior lattice cage;

a material injection port disposed at the exterior lattice cage and projecting into the interior porous lattice structure; and a plurality of material propagation channels disposed within the interior porous lattice structure and extending to the exterior lattice cage, wherein the interior porous lattice structure is organized by a variable density from the exterior lattice cage to a central-most point of the porous fusion device, wherein the variable density comprises a gradual decrease in density from the exterior lattice cage to the central-most point of the porous fusion device, wherein the porous fusion device is configured to be backfilled with a material following insertion into a patient.

9. The porous fusion device of claim 8, wherein the plurality of material propagation channels comprises at least one horizontal material propagation channel fluidly coupled to at least one vertical material propagation channel.

10. The porous fusion device of claim 9, wherein the at least one vertical material propagation channel extends through the exterior frame.

11. The porous fusion device of claim 10, wherein the material injection port further comprises a threaded channel having a first threaded portion and a second threaded portion with a break disposed therebetween.

12. The porous fusion device of claim 8, wherein the plurality of material propagation channels comprises at least one horizontal material propagation channel fluidly coupled to at least one radially extending material propagation channel.

13. The porous fusion device of claim 8, wherein the plurality of material propagation channels is arranged to direct the material towards the two or more tissues.

14. The porous fusion device of claim 8, further comprising a backstop at least partially enclosing the exterior lattice cage, the backstop configured to retain injected material within the porous fusion device.

15. A method of instructing use of a porous fusion device, comprising:

providing the porous fusion device comprising:

an exterior frame;

an exterior lattice cage disposed within the exterior frame;

an interior porous lattice structure disposed within the exterior lattice cage, wherein the interior porous lattice structure of the porous fusion device is organized by a gradual decrease in density from the exterior lattice cage to a central-most point of the porous fusion device; and a material injection port disposed at the exterior lattice cage and projecting into the interior porous lattice structure;

instructing attaching a material injection tool to the material injection port of the porous fusion device;

instructing inserting the porous fusion device between at least two biological tissues;

instructing filling at least part of the porous fusion device with a material via the material injection tool; and instructing disconnecting the material injection tool from the material injection port on the porous fusion device.

16. The method of claim 15, wherein the material injection port of the porous fusion device further comprises a threaded channel comprising a first threaded portion and a second threaded portion having a break disposed therebetween.

17. The method of claim 15, wherein instructing filling at least part of the porous fusion device with the material occurs prior to instructing inserting the porous fusion device between the at least two biological tissues.

18. The method of claim 15, wherein the material injected into the porous fusion device is bone graft material.

19. The method of claim 15, wherein the porous fusion device further comprises a backstop disposed opposite of the material injection port and configured to retain the material injected into the porous fusion device.

20. The method of claim 15, further comprising instructing adjustment of a viscosity of the material based at least in part on the density of the interior porous lattice structure.

* * * * *